United States Patent [19]

Yamada et al.

[11] Patent Number: 5,224,480
[45] Date of Patent: Jul. 6, 1993

[54] ULTRASONIC IMAGING APPARATUS INDICATING DISPERSION OF CHARACTERISTIC PARAMETER OF MEDIUM

[75] Inventors: Isamu Yamada; Akira Shiba, both of Kawasaki; Shinichi Amemiya, Yokohama; Keiichi Murakami, Kawasaki; Takaki Shimura, Machida, all of Japan

[73] Assignee: Fujitsu Limited, Kawasaki, Japan

[21] Appl. No.: 707,741

[22] Filed: May 30, 1991

[30] Foreign Application Priority Data

May 31, 1990 [JP] Japan ................. 2-142355

[51] Int. Cl.⁵ .............................................. A61B 8/00
[52] U.S. Cl. .............................................. 128/660.06
[58] Field of Search ................... 128/661.06–661.10

[56] References Cited

U.S. PATENT DOCUMENTS

| | | | |
|---|---|---|---|
| 4,501,277 | 2/1985 | Horgo | 128/660.07 X |
| 4,662,380 | 5/1987 | Riley | 128/660.07 |
| 4,817,015 | 3/1989 | Insana et al. | 364/507 |
| 4,852,577 | 8/1989 | Smith et al. | 128/660.07 |
| 4,855,911 | 8/1989 | Lele et al. | 128/660.06 X |
| 4,873,869 | 10/1989 | Fink | 128/660.07 X |

FOREIGN PATENT DOCUMENTS 0150997 8/1985 European Pat. Off. .
0154869 9/1985 European Pat. Off. .
62-109553 5/1987 Japan .

OTHER PUBLICATIONS

Greene, F. M. et al. "Computer-Based Pattern Recognition of Carotid Arteryaloses," UTS in Med. & Biol. vol. 8 No. 2 pp. 161-176 1987.

Primary Examiner—Francis Jaworski
Attorney, Agent, or Firm—Staas & Halsey

[57] ABSTRACT

An ultrasonic imaging apparatus for obtaining a two-dimensional distribution of a predetermined characteristic parameter of a medium of the ultrasound at various points in a plane. The apparatus contains a unit for designating a region of interest in said plane, and a unit for obtaining and indicating statistical information on a dispersing characteristic of said predetermined characteristic parameter of the medium at the various points in the region of interest of said plane. In addition, the apparatus contains a unit for obtaining and indicating a recent history of the dispersing characteristics during the operation of obtaining the two-dimensional distributions which are most recently carried out. Further, the apparatus contains a unit for obtaining and indicating the plane for which the minimum standard deviation is obtained, and a unit for indicating the two-dimensional distribution for the plane.

24 Claims, 10 Drawing Sheets

ULTRASONIC IMAGING APPARATUS INDICATING DISPERSION OF CHARACTERISTIC PARAMETER OF MEDIUM

BACKGROUND OF THE INVENTION (1) Field of the Invention

The present invention relates to an ultrasonic imaging apparatus which functions to display an image of a two-dimensional distribution of a tissue characterization parameter of a tissue, for example, an ultrasonic attenuation coefficient, in a realtime mode.

In the field of the ultrasonic diagnosis, the two-dimensional distribution of the tissue characterization parameters, for example, an ultrasonic attenuation coefficient, an ultrasonic reflection coefficient, an elasticity parameter, are used to diagnose a condition of the tissue. For example, the value of the ultrasonic attenuation coefficient of tissue of a liver suffering from hepatitis is small compared with a normal tissue, and the value of the ultrasonic attenuation coefficient of a fatty liver is large compared with a normal tissue. Since high accuracy is required in ultrasonic diagnosis, the tissue characterization parameters must be determined precisely.

(2) Description of the Related Art

Conventionally, the ultrasonic imaging apparatus which functions to display an image of a two-dimensional distribution of a tissue characterization parameter of a tissue in a realtime mode is disclosed in the Japanese Unexamined Patent Publication No.62-109553, and the U.S. Pat. No.4,836,210 of Shiba et al, dated Jun. 6, 1989.

In ultrasonic imaging apparatuses, a pulsed beam of an ultrasound is generated to inject the beam into a tissue in a certain direction, and ultrasound which is reflected at various depths of the tissue in the same direction are detected. The direction of the pulsed ultrasound is scanned so that a plane is scanned by the pulsed ultrasound during one plane scan cycle. Thus, a two-dimensional distribution of the tissue characterization parameter on the plane (cross section of the tissue) is obtained. The above injection and detection of the ultrasound is carried out through an ultrasonic transducer array. The operator (doctor) applies a probe containing the transducer array on a skin of a human body to diagnose the condition of the tissue under the skin.

However, the obtained values of the above tissue characterization parameters fluctuate due to subtle movements of the probe or the tissue which is subject to the diagnosis. Further, for example, the values of the ultrasonic attenuation coefficient, which are obtained as above, greatly vary when a structure which is different from the tissue which is to be diagnosed, e.g., a vascular tract, exists in the scanned cross section. Generally, it is considered that the obtained values of the tissue characterization parameters are significant only when the obtained values are stable. Thus, generally, the values of the tissue characterization parameters must be obtained on a cross section of the tissue where the obtained values are stable. Nevertheless, conventionally, it is difficult for the operator to determine whether or not an obtained value of a tissue characterization parameter is stable. Therefore, in conventional ultrasonic imaging apparatuses, the credibility of the obtained values of the tissue characterization parameters is low.

SUMMARY OF THE INVENTION

An object of the present invention is to provide an ultrasonic imaging apparatus whereby an operator can easily determine stability of a value of a tissue characterization parameter which is obtained from the apparatus.

Another object of the present invention is to provide an ultrasonic imaging apparatus whereby an operator can easily determine a cross section which gives the most stable value of a tissue characterization parameter which is to be obtained, among a plurality of cross sections from which values of the tissue characterization parameter are most recently obtained.

According to the aspect of the present invention, there is provided an ultrasonic imaging apparatus which comprises: an ultrasound generating unit for generating a pulsed ultrasound to externally output in a certain direction for each output of the pulsed ultrasound; an ultrasound detecting unit for detecting reflected ultrasound which is generated by reflection of the pulsed ultrasound at various points outside of the ultrasonic imaging apparatus in the above direction, and reaches the ultrasound detecting unit after the above output of pulsed ultrasound; a scanning unit for scanning the direction of the pulsed ultrasound which is generated by the ultrasound generating unit and the reflected ultrasound which reaches the ultrasound detecting unit, so that a plane is scanned by the pulsed ultrasound which is generated by the ultrasound generating unit during one plane scan cycle; a two-dimensional distribution obtaining unit for obtaining a two-dimensional distribution of a predetermined characteristic parameter of a medium of the ultrasound at various points in the plane, wherein distances from the ultrasound detecting unit to the various points in the plane at which the reflected ultrasound are generated, are determined by measuring times which elapsed after the pulsed ultrasound is output from the ultrasound generating unit until the corresponding reflected ultrasound are detected in the ultrasound detecting unit; a region of interest designating unit for designating a region of interest in the plane; and a statistic information obtaining unit for obtaining statistic information on a dispersing characteristic of the predetermined characteristic parameter of the medium at the various points in the region of interest of the plane.

The ultrasonic imaging apparatus further comprises a statistic information indicating unit for indicating the statistic information.

The ultrasonic imaging apparatus further comprises a statistic information storing unit for storing the statistic information for a predetermined number of planes.

The ultrasonic imaging apparatus further comprises a stored statistic information indicating unit for indicating the statistic information which is stored in the statistic information storing unit.

The ultrasonic imaging apparatus further comprises a two-dimensional distribution storing unit for storing the two-dimensional distributions of the predetermined characteristic parameter of the medium for a predetermined number of planes.

The ultrasonic imaging apparatus further comprises a stored distribution indicating unit for indicating the two-dimensional distributions which are stored in the two-dimensional distribution storing unit.

The statistic information storing unit stores the statistic information for a predetermined number of planes for which the two-dimensional distribution of the predetermined characteristic parameter of the medium are most recently obtained by the two-dimensional distribution obtaining unit.

The ultrasonic imaging apparatus further comprises a stored statistic information indicating unit for indicating the statistic information which is stored in the statistic information storing unit.

The ultrasonic imaging apparatus further comprises a two-dimensional distribution storing unit for storing the two-dimensional distributions of the predetermined characteristic parameter of the medium for a predetermined number of planes which are most recently obtained by the two-dimensional distribution obtaining unit.

The ultrasonic imaging apparatus further comprises a stored distribution indicating unit for indicating one of the two-dimensional distributions which are stored in the two-dimensional distribution storing unit.

The ultrasonic imaging apparatus further comprises a storage freezing unit for freezing an operation renewing the statistic information storing unit and the two-dimensional distribution storing unit.

The ultrasonic imaging apparatus further comprises a frozen plane designating unit for designating one of the planes for which the statistic information and the two-dimensional distributions are stored in the statistic information storing unit and the two-dimensional distribution storing unit, respectively, after the statistical information storing means and the two-dimensional distribution storing means are frozen.

The ultrasonic imaging apparatus further comprises a designated information indicating unit for indicating the statistic information and the two-dimensional distribution for the plane which are designated by the frozen plane designating unit.

The ultrasonic imaging apparatus further comprises: a plane designating unit for designating one of the planes for which the statistic information and the two-dimensional distributions are stored in the statistic information storing unit and the two-dimensional distribution storing unit, and a history information indicating unit for indicating a recent history of the statistic information from a plane for which the two-dimensional distribution is most recently obtained, to the plane which is designated by the plane designating unit.

When the statistic information obtaining unit comprises a standard deviation obtaining unit for obtaining a standard deviation of the predetermined characteristic parameter of the medium at the various points in the region of interest of the plane, the ultrasonic imaging apparatus may further comprise: a minimum standard deviation plane determining unit for determining a plane for which the minimum standard deviation is obtained by the standard deviation obtaining unit, among planes for which the statistic information and the two-dimensional distributions are stored in the statistic information storing unit and the two-dimensional distribution storing unit; and a minimum standard deviation plane indicating unit for indicating the plane for which the minimum standard deviation is obtained by the standard deviation obtaining unit.

The ultrasonic imaging apparatus further comprises an optimum two-dimensional distribution indicating unit for indicating a two-dimensional distribution for the plane for which the minimum standard deviation is obtained by the standard deviation obtaining unit.

The statistic information includes an average of the predetermined characteristic parameter of the medium at the various points in the region of interest of the plane.

The statistic information includes a standard deviation of the predetermined characteristic parameter of the medium at the various points in the region of interest of the plane.

The statistic information includes a skewness of a frequency distribution of values of the tissue characterization parameter which was obtained in the parameter calculation circuit within the region of interest of the predetermined characteristic parameter of the medium at the various points in the region of interest of the plane.

The statistic information includes a kurtosis of a frequency distribution of the values of the tissue characterization parameter of the medium at the various points in the region of interest of the plane.

The ultrasonic imaging apparatus further comprises: a region of interest redesignating unit for designating a region of interest other than the region of interest which is designated by the region of interest designating unit, in the plane; and a statistic information reobtaining unit for obtaining statistic information on a dispersing characteristic of the predetermined characteristic parameter of the medium at the various points in the region of interest which is designated by the region of interest redesignating unit.

DESCRIPTION OF THE PREFERRED EMBODIMENTS

Figure 1:
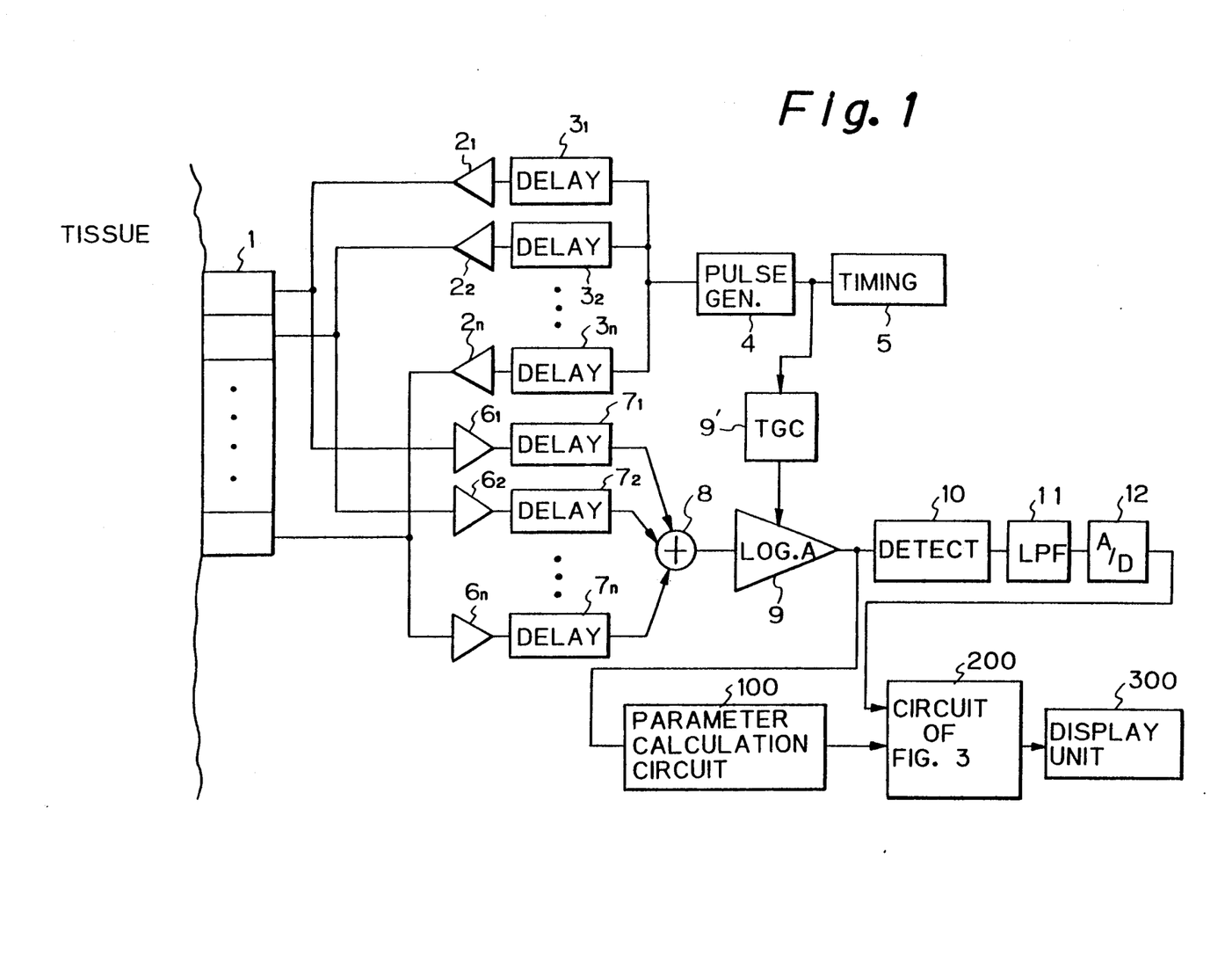
FIG. 1 is a block diagram showing a construction of the embodiment of the present invention.

FIG. 1

FIG. 1 is a block diagram showing a construction of the embodiment of the present invention. In FIG. 1, reference numeral 1 denotes an ultrasonic transducer array, $2_1, 2_2, 2_3, \ldots 2_n$ and $6_1, 6_2, 6_3, \ldots 6_n$ each denote an amplifier, $3_1, 3_2, 3_3, \ldots 3_n$ and $7_1, 7_2, 7_3, \ldots 7_n$ each denote a delay circuit, 4 denotes a pulse generator, 5 denotes a timing generator, 8 denotes a summing amplifier, 9 denotes a LOG amplifier, 9' denotes a time gain control circuit, 10 denotes a detector, 11 denotes a low pass filter, 12 denotes an analog to digital converter, 100 denotes a parameter calculation circuit, 200 denotes a characteristic portion of the embodiment of the present invention, and 300 denotes a display unit.

The timing generator 5 generates a timing signal at a constant rate, and the pulse generator 4 generates a pulse signal to generate an ultrasound pulse. Each delay circuit $3_i$ and $7_i (i=1, 2, \ldots n)$ is connected in series to a corresponding one of the amplifiers $2_i$ and $6_i (i=1, 2, \ldots n)$. The pulse signal is input in parallel to the respective series connections of the delay circuits $3_i (i=1, 2, \ldots n)$ and the amplifiers $2_i (i=1, 2, \ldots n)$. The ultrasonic transducer array 1 comprises a plurality of transducer elements. Each transducer element comprises a piezo-electric element which converts an electric signal to a mechanical deformation to generate an ultrasound, and generates an electric signal when the element receives an ultrasound. The transducer array 1 is manually applied to a skin over a region of tissue of the human body in which a doctor is interested, to diagnose the region. The above outputs of the series connections parallel connection are respectively applied to the plurality of transducer elements of the ultrasonic transducer array 1. Delay times in the above delay circuits $3_i (i=1, 2, \ldots n)$ are controlled so that the ultrasound which is generated at the above transducer elements are synthesized to form an ultrasound beam directed in a certain direction for each cycle of the output of the ultrasound, and the direction is moved to scan a cross section of the tissue for each scanning cycle.

The electric signals which are output from the plurality of transducer elements are respectively input in parallel into the series connections of the delay circuits $7_i (i=1, 2, \ldots n)$ and the amplifiers $6_i (i=1, 2, \ldots n)$. The outputs of the series connections of the delay circuits $7_i (i=1, 2, \ldots n)$ and the amplifiers $6_i (i=1, 2, \ldots n)$ are summed in the summing amplifier 8 to apply the summed signal to the LOG amplifier 9. Delay times in the above delay circuits $7_i (i=1, 2, \ldots n)$ are controlled so that the summed signal corresponds to ultrasound which is received in the transducer array 1 from the above direction of the above ultrasound beam which is generated in the transducer array 1, and the direction is moved to scan a cross section of the tissue for each scanning cycle, synchronized with the above scanning operation by the delay circuits $3_i (i=1, 2, \ldots n)$. The LOG amplifier 9 amplifies the summed signal. The gain of the LOG amplifier 9 is controlled by the time gain control circuit 9' so that the gain of the LOG amplifier 9 is increased with a time which is elapsed from each time of the above generation of the ultrasound in the transducer array 1 in accordance with a logarithm line. The output of the LOG amplifier 9 is applied in parallel to the detector 10 and the parameter calculation circuit 100.

The envelope of the above output of the LOG amplifier 9 is detected in the detector 10, and the detected signal is input into the low pass filter 11. The output of the low pass filter 11 corresponds to image data of ultrasonograph. The output of the low pass filter 11 is converted to a digital form by the analog to digital converter 12. The digital data is supplied to the characteristic portion 200.

Figure 2:
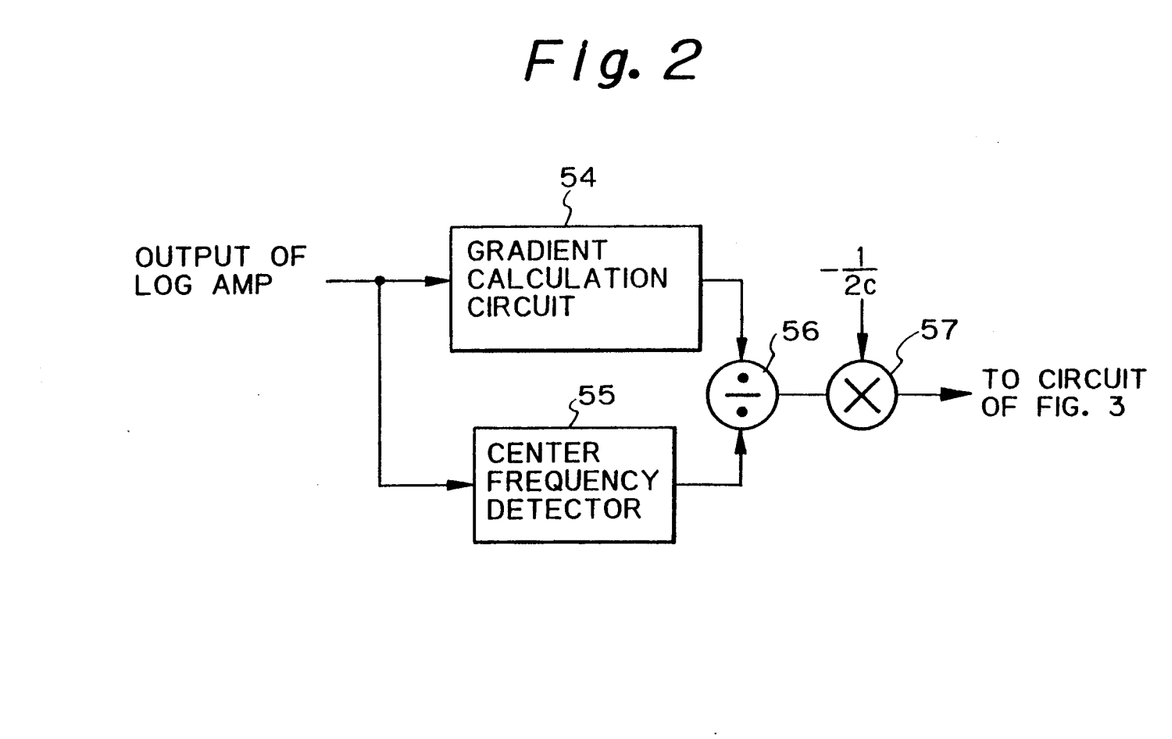
FIG. 2 is a block diagram showing a construction of an example of the parameter calculation circuit 100 in FIG. 1.

Parameter Calculation Circuit (FIG. 2)

FIG. 2 is a block diagram showing a construction of an example of the parameter calculation circuit 100 in FIG. 1. In FIG. 2, reference numeral 54 denotes a gradient calculation circuit, 55 denotes a center frequency detector, 56 denotes a divider, and 57 denotes a multiplier.

The gradient calculation circuit 54 obtains a gradient of an envelope of the above output of the LOG amplifier 9 in a digital form, and the center frequency detector 55 detects a center frequency of the output of the LOG amplifier 9 in a digital form. The divider 56 divides the output of the gradient calculation circuit 54 by the output of the center frequency detector 55, and the multiplier 57 multiplies the output of the divider 56 by a constant $-\frac{1}{2}c$ to obtain the ultrasonic attenuation coefficient. The obtained ultrasonic attenuation coefficient is supplied to the above characteristic portion 200. The detail of the construction for obtaining the ultrasonic attenuation coefficient is disclosed in the Japanese Unexamined Patent Publication No. 62-109553. The parameter calculation circuit 100 may be another construction for obtaining an ultrasonic reflection coefficient, or another elasticity parameter. These constructions for obtaining the ultrasonic reflection coefficient, and the other elasticity parameters are conventionally known.

Figure 3:
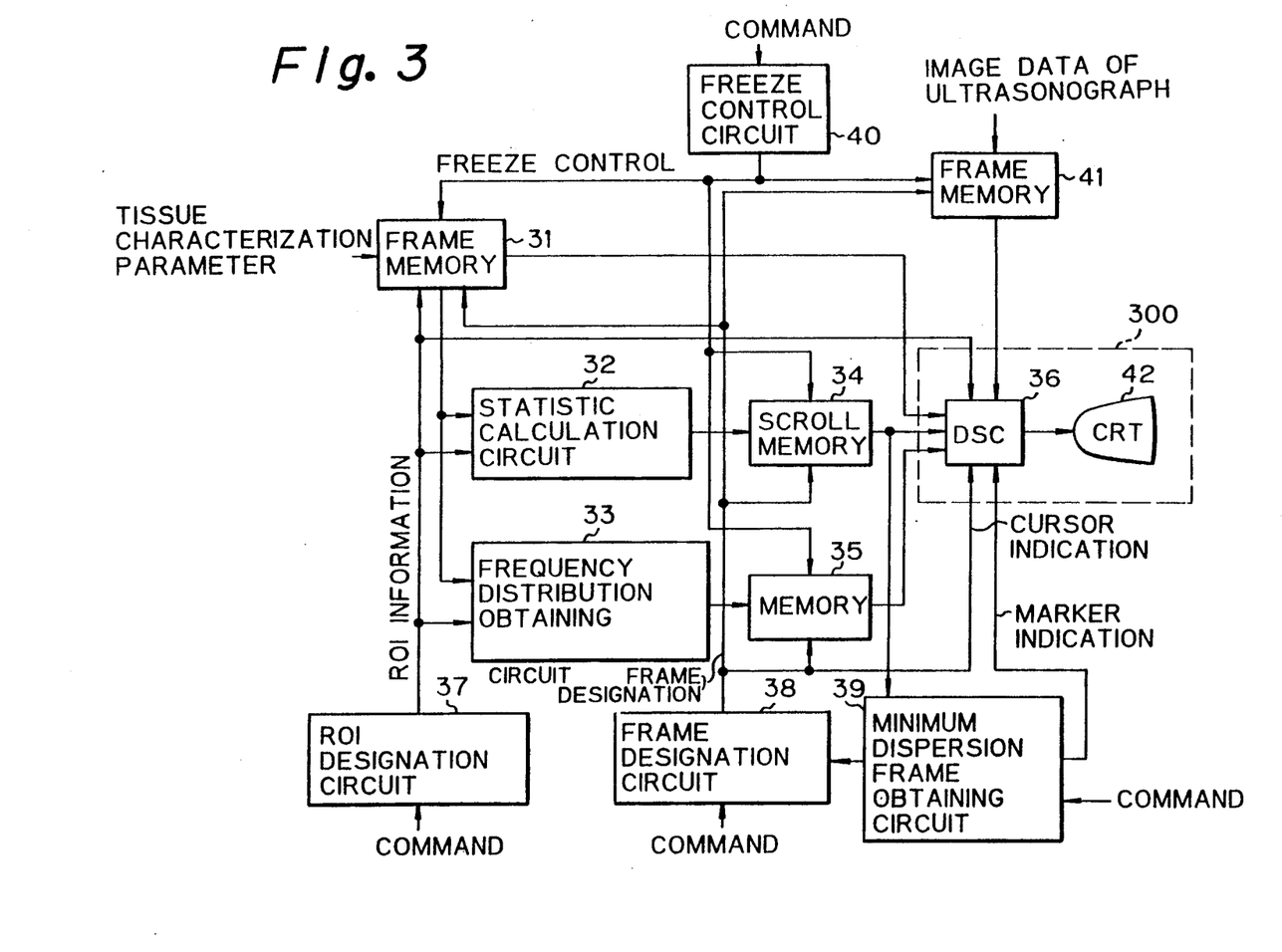
FIG. 3 is a block diagram showing a construction of the characteristic portion of the embodiment of the present invention.

Characteristic Portion (FIG. 3)

FIG. 3 is a block diagram showing a construction of the characteristic portion of the embodiment of the present invention. In FIG. 3, reference numeral 31 denotes a frame memory for the two-dimensional distribution of a tissue characterization parameter, 32 denotes a statistic calculation circuit, 33 denotes a frequency distribution obtaining circuit, 34 denotes a scroll memory, 35 denotes a memory, 36 denotes a digital scan converter, 37 denotes a region of interest designation circuit, 38 denotes a frame designation circuit, 39 denotes a minimum dispersion frame obtaining circuit, 40 denotes a freeze control circuit, 41 denotes a frame memory for image data of ultrasonograph, and 42 denotes a CRT.

The above digital image data of ultrasonograph is stored in the frame memory 41, and the above digital tissue characterization parameter is stored in the frame memory 31. These frame memories respectively hold the data of a plurality of frames which have been most recently observed. The statistic calculation circuit 32 obtains statistic information on a dispersing characteristic of the characteristic parameter of the tissue at the various points in a region of interest of each cross section. The region of interest is designated by the region of interest designation circuit 37 as explained later.

Statistic Information

The statistic information is, for example, an average of the values of the tissue characterization parameter which was obtained in the parameter calculation circuit 100 within the region of interest in each cross section, a standard deviation of the values of the tissue characterization parameter which was obtained in the parameter calculation circuit 100 within the region of interest in each cross section, a skewness of a frequency distribution of the values of the tissue characterization parameter which was obtained in the parameter calculation circuit 100 within the region of interest in each cross section, or the kurtosis of a frequency distribution of the values of the tissue characterization parameter which was obtained in the parameter calculation circuit 100 within the region of interest in each cross section. When the values of the tissue characterization parameter in the region of interest are denoted by $x_i (i=1,2,\ldots N)$ where N denotes the number of the obtained values in the region of interest.

The average m is obtained by the following equation (1).

$$m = (1/N) \cdot \sum_{i=1}^{N} x_i \quad (1)$$

The variance $\sigma^2$ is obtained by the following equation (2).

$$\sigma^2 = (1/N) \cdot \sum_{i=1}^{N} x_i^2 - m^2 \quad (2)$$

The standard deviation $\sigma$ is obtained by the following equation (3).

$$\sigma = \sqrt{\sigma^2} \quad (3)$$

The third order center moment $\mu_3$ is obtained as the following equation (4).

$$\mu_3 = (1/N) \cdot \sum_{i=1}^{N} x_i^3 - (3m/N) \cdot \sum_{i=1}^{N} x_i^2 + 2m^3 \quad (4)$$

The fourth order center moment $\mu_4$ is obtained by the following equation (5).

$$\mu_4 = (1/N) \cdot \sum_{i=1}^{N} x_i^4 - (4m/N) \cdot \sum_{i=1}^{N} x_i^3 + (6m^2/N) \cdot \sum_{i=1}^{N} x_i^2 - 3m^4 \quad (5)$$

The skewness S of the frequency distribution of the values of the tissue characterization parameter in the region of interest indicates asymmetry of the frequency distribution, and is obtained by the following equation (6).

$$S = \mu_3/\sigma^3 \quad (6)$$

The kurtosis K of the frequency distribution of the values of the tissue characterization parameter in the region of interest indicates flatness of the frequency distribution, and is obtained by the following equation (6).

$$K = \mu_4/\sigma^4 - 3 \quad (7)$$

The results of the statistic calculations as above are input into the scroll memory 34 for each frame (cross section). The scroll memory 34 stores the statistic information for a predetermined number of frames which are most recently observed.

Figure 4:
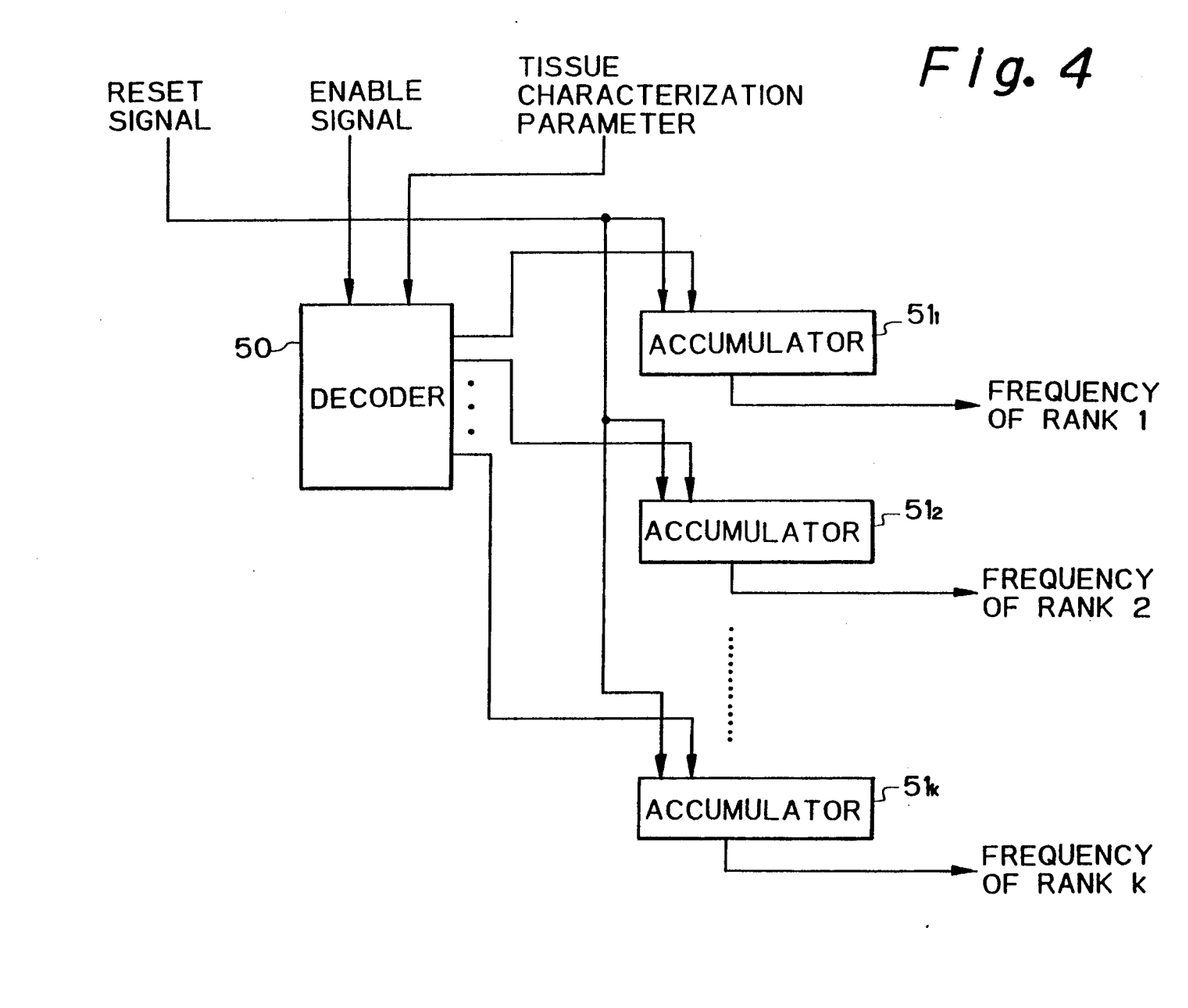
FIG. 4 is a block diagram showing a construction of the frequency distribution obtaining circuit 33 in FIG. 3.

Frequency Distribution Obtaining Circuit (FIG. 4)

The frequency distribution obtaining circuit 33 obtains a frequency distribution of the values of the tissue characterization parameter in the region of interest in each cross section. FIG. 4 is a block diagram showing a construction of the frequency distribution obtaining circuit 33 in FIG. 3. In FIG. 4, reference numeral 50 denotes a decoder, and $51_1, 51_2, 51_3, \ldots 51_n$ each denote an accumulator.

Figure 5:
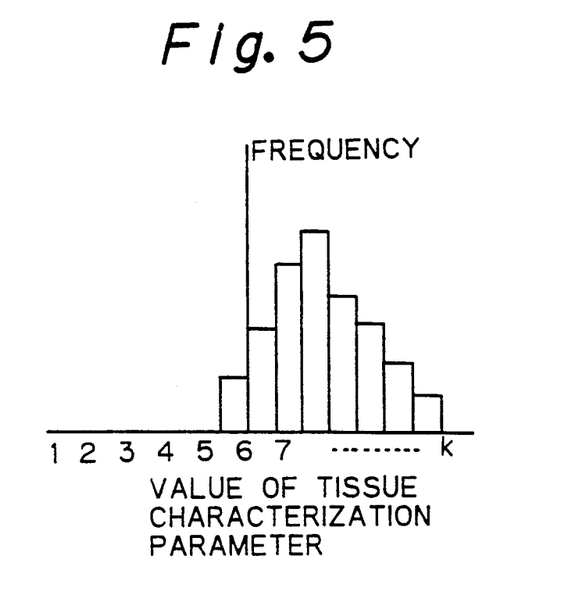
FIG. 5 is a histogram showing a frequency distribution of values of a tissue characterization parameter in a region of interest.

The values of the tissue characterization parameter are sorted into a plurality of ranks (ranges of the values) to obtain a histogram of the frequency distribution. The accumulators $51_1, 51_2, 51_3, \ldots 51_n$ are provided for the respective ranks. The decoder 50 receives respective values of the tissue characterization parameter which are stored in the frame memory 31. The decoder 50 has a plurality of outputs corresponding to the plurality of ranks to realize the function of the sorting. One of the outputs of the decoder 50 corresponding to one of the ranks to which the received value is to be sorted, becomes active when the enable signal is active. The enable signal is generated by the region of interest designation circuit 37, and is made active when values of the tissue characterization parameter in the region of interest are output from the frame memory 31. A reset signal is applied to the plurality of accumulators $51_1, 51_2, 51_3, \ldots 51_n$ when the accumulators should be reset. The accumulation is carried out for example, for each scanning cycle (each cross section), or for a predetermined number of successive scanning cycles. FIG. 5 is an example histogram showing a frequency distribution of values of the tissue characterization parameter in the region of interest. The above obtained frequency distribution is input into the memory 35 for each frame (cross section). The memory 35 stores the data of the frequency distributions for a predetermined number of frames which are most recently observed.

Figure 6:
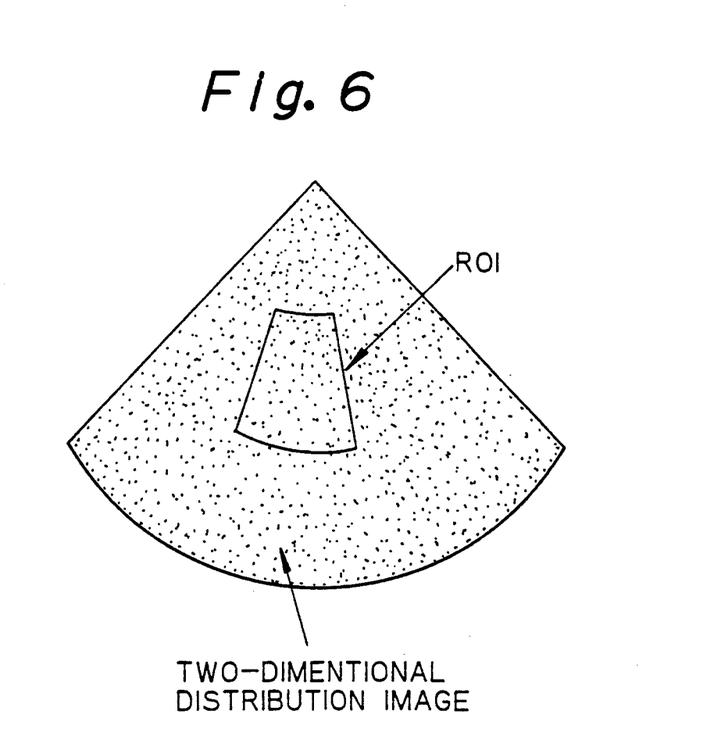
FIG. 6 is a diagram showing an example of the display of the two-dimensional distribution of detected values of a tissue characterization parameter and an indication of the designated region of interest.

FIG. 6

FIG. 6 is a diagram showing an example of the display of the two-dimensional distribution of detected values of a tissue characterization parameter and an indication of the designated region of interest. Viewing the display, the operator can designate a desired region of interest, for example, by a pointing device. The region of interest designation circuit 37 controls the operation reading the values of the tissue characterization parameter from the frame memory 31 and the operation writing the values into the statistic calculation circuit 32 and the frequency distribution obtaining circuit 33 by supplying corresponding addresses and reading and writing signals. The technique of designating a region of interest is well-known.

Indication of History of Statistics (FIGS. 3, 7, 8, 9, and 10)

Figure 7:
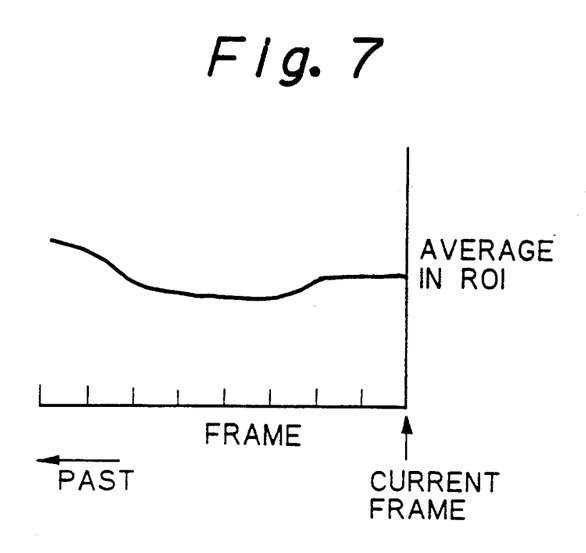
FIG. 7 is a diagram showing an example indication of a recent history of the average of detected values of a tissue characterization parameter in a region of interest.
Figure 8:
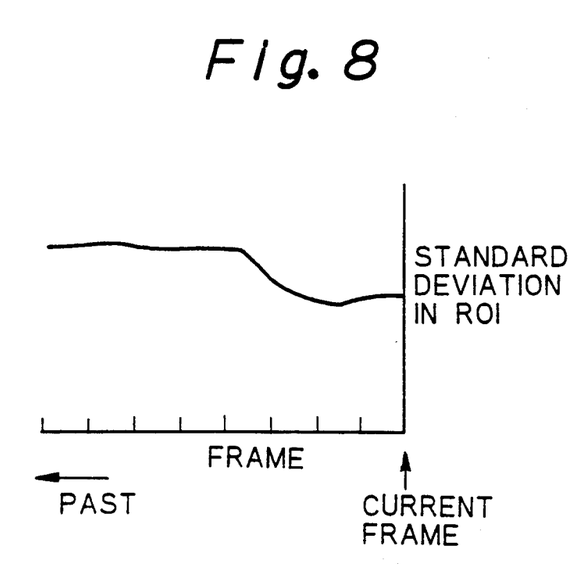
FIG. 8 is a diagram showing an example indication of a recent history of the standard deviation of detected values of a tissue characterization parameter in a region of interest.
Figure 9:
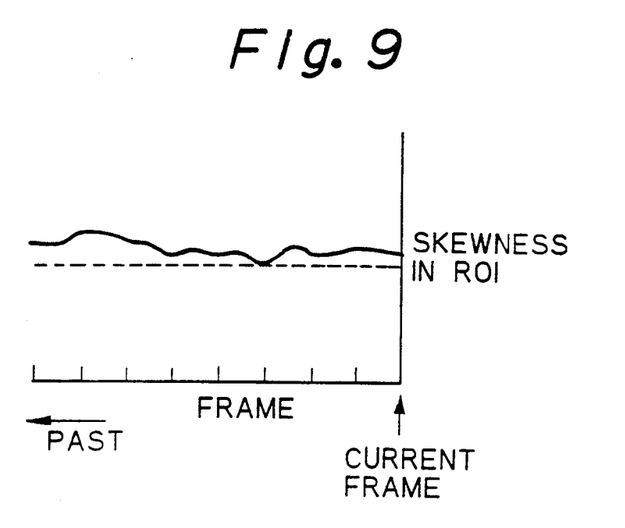
FIG. 9 is a diagram showing an example indication of a recent history of the skewness of a frequency distribution of detected values of the tissue characterization parameter in a region of interest.
Figure 10:
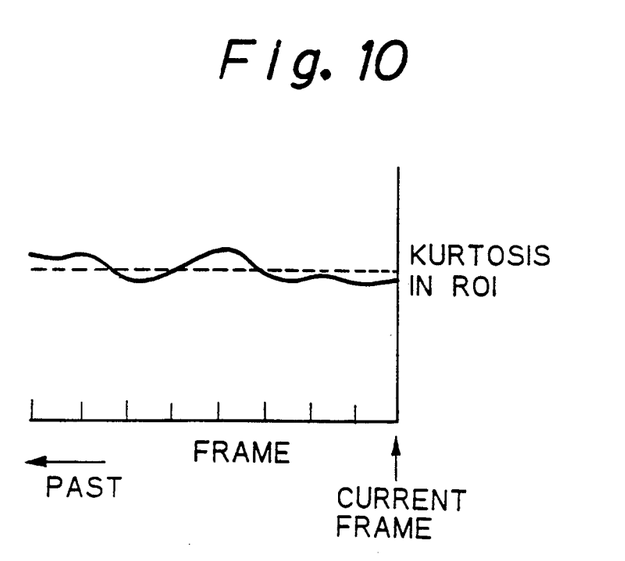
FIG. 10 is a diagram showing an example indication of a recent history of the kurtosis of a frequency distribution of detected values of the tissue characterization parameter in a region of interest.
Figure 11:
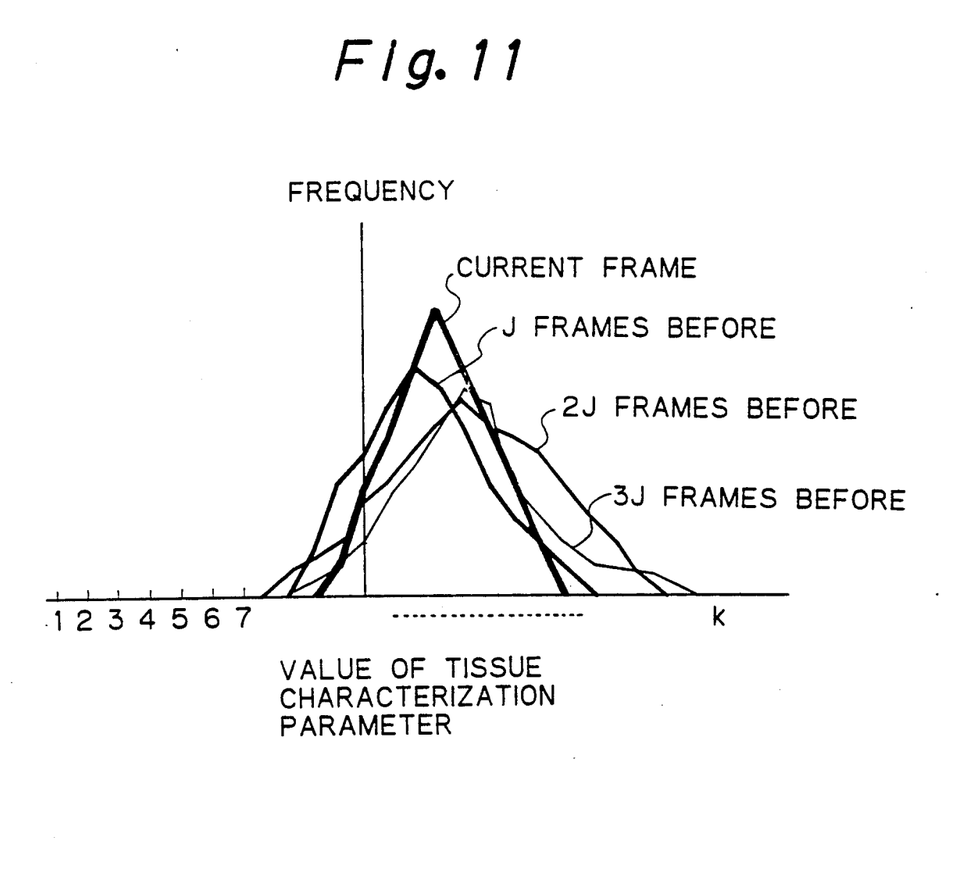
FIG. 11 is a diagram showing an example indication of a recent history of the frequency distribution of detected values of a tissue characterization parameter in a region of interest.

In an indication mode, a recent history of one or more of the aforementioned statistic information in a predetermined number of successive frames ending with a current frame is indicated in a real time mode as shown in FIGS. 7 to 11. The above history data is supplied from the scroll memory 34 and the memory 35. In the above indication, each statistic information in the history may be calculated for a predetermined number of successive frames instead of one frame. FIG. 7 is a diagram showing an example indication of a recent history of an average of a frequency distribution of detected values of a tissue characterization parameter in a region of interest, FIG. 8 is a diagram showing an example indication of a recent history of a standard deviation of a frequency distribution of detected values of a tissue characterization parameter in a region of interest, FIG. 9 is a diagram showing an example indication of a recent history of the skewness of a frequency distribution of detected values of the tissue characterization parameter in a region of interest, FIG. 10 is a diagram showing an example indication of a recent history of the kurtosis of a frequency distribution of detected values of the tissue characterization parameter in a region of interest, and FIG. 11 is a diagram showing an example indication of a recent history of the frequency distribution of detected values of a tissue characterization parameter in a region of interest. In FIG. 11, the lines for the frequency distributions of the different frames may be indicated by the different types of lines, respectively, for example, by using different colors. The operator can view the above indication while manipulating the probe. Therefore, for example, the operator can recognize whether or not a most recently variation of a position of the probe gives a better (more stable and credible) result, and can avoid to take unstable data based on the above history indications.

Figure 12:
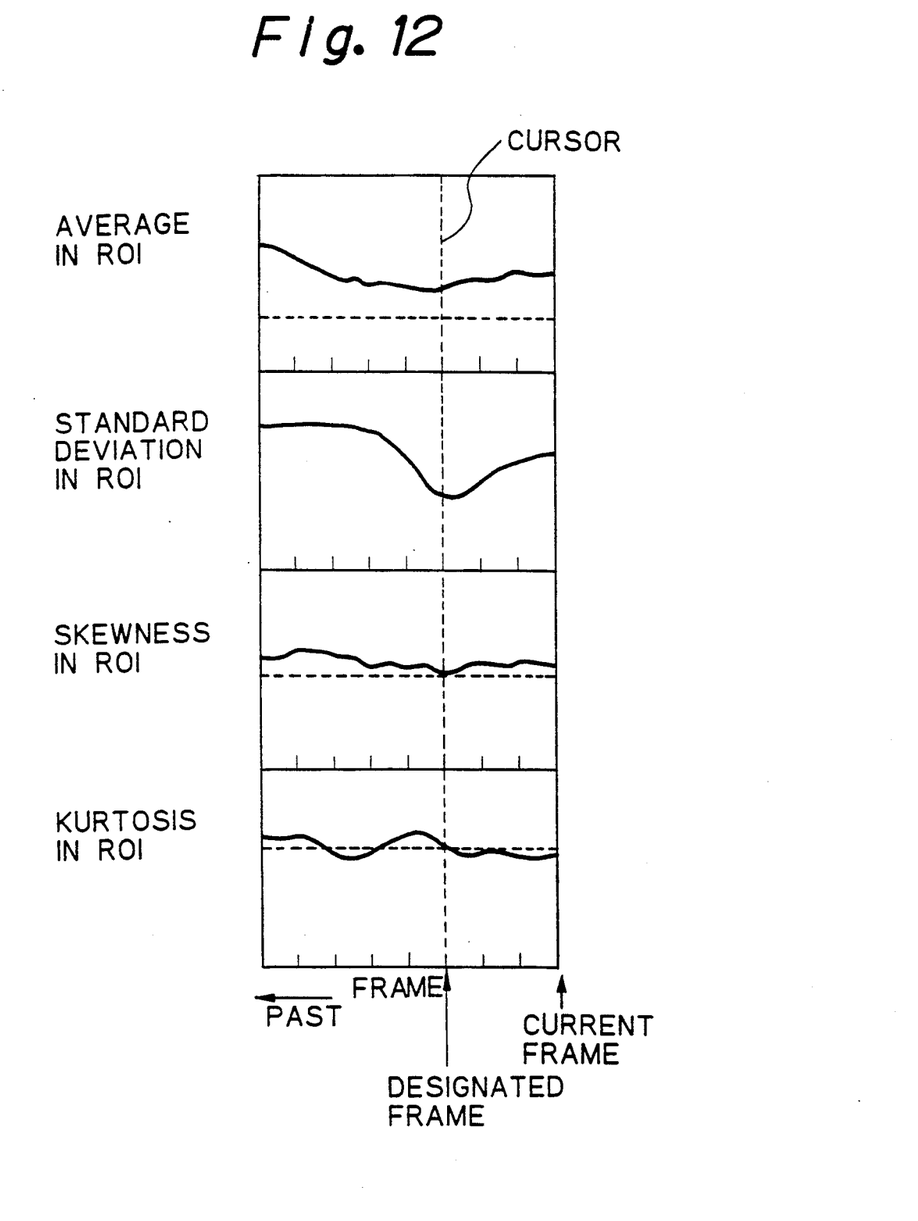
FIG. 12 is a diagram showing an example indication in an operation designating a frame by an operator using a cursor.

Freeze Control and Frame Designation (FIGS. 3 and 12)

When the operator finds in the above history indication that credible data has been obtained, the operator can freeze an operation renewing the contents of the scroll memory 34 and the memory 35, and thus, can freeze the history indication. The freezing operation can be carried out through the freeze control circuit 40. When the freeze control circuit 40 receives a command to effect the freeze operation, the freeze control circuit 40 supplies a freeze control signal to the frame memories 31 and 41, the scroll memory 34, and the memory 35 to freeze these elements, as shown in FIG. 3.

FIG. 12 is a diagram showing an example indication in an operation designating a frame by an operator using a cursor. As shown in FIG. 12, the operator can designate one of the frames for which the history of the statistic information is indicated, based on the indication, by moving a cursor to the frame in the history indication using a pointing device (not shown). This operation is realized through the frame designation circuit 38. Responding to the designation by the operator, the frame designation circuit 38 can control the frame memories 31 and 41, the scroll memory 34, and the memory 35, so that these memories output contents thereof regarding the designated frame, to the digital scan converter 36. Further, the frame designation circuit 38 can send the information on the designated frame to the digital scan converter 36 so that the above cursor indication is realized.

Further, the aforementioned region of interest designation circuit 37 can be operated again to reobtain statistic information on the dispersing characteristic of the predetermined characteristic parameter in a region of interest which is different from the region of interest which was first designated. Redesignating the new region of interest through the region of interest designation circuit 37 after freezing the above memories in FIG. 3, the above statistical information can be obtained by using the frozen data of the tissue characterization parameter, and operating the statistic calculation circuit 32 and/or the frequency distribution obtaining circuit 33.

Figure 13:
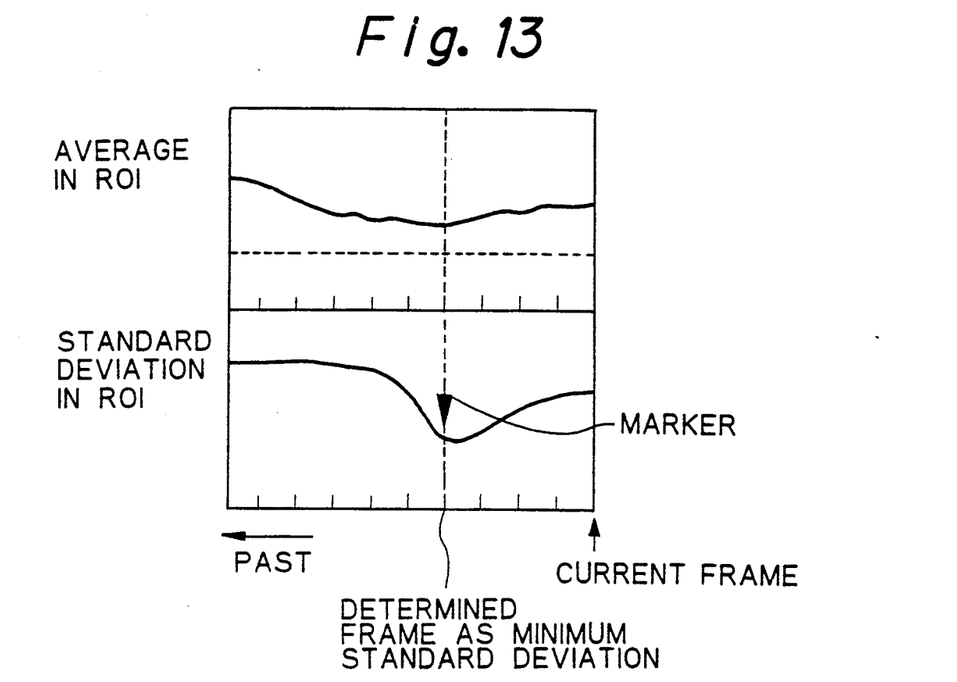
FIG. 13 is a diagram showing an example indication of a frame which is designated as a frame which gives the minimum standard deviation among a plurality of frames which has been most recently observed.
Figure 14:
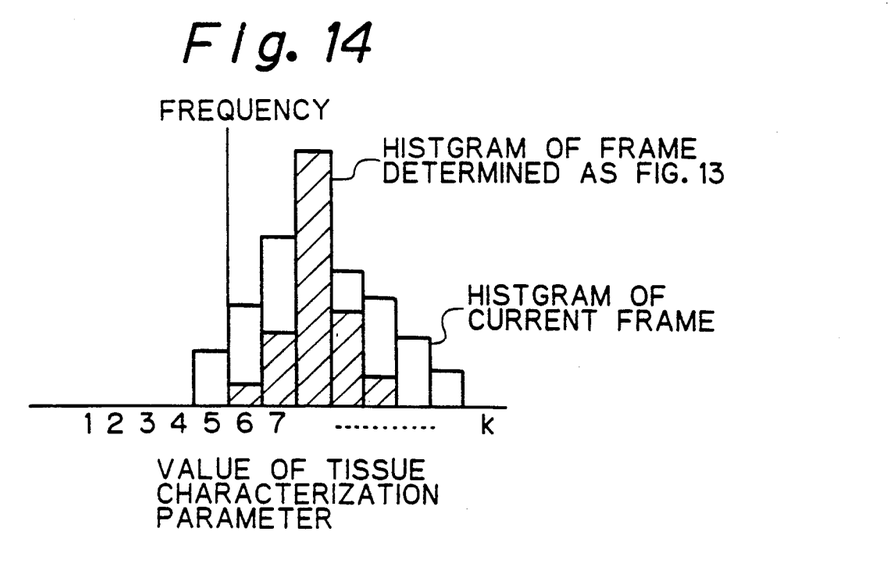
FIG. 14 is a diagram showing an example indication of a frequency distribution of values of a tissue characterization parameter in a current frame, where a frequency distribution of values of the tissue characterization parameter in the frame which gives the minimum standard deviation is superimposed on the frequency distribution in the current frame.

Calculation of Most Stable Frame (FIGS. 3, 13, and 14)

The most stable frame among a plurality of frames which have been most recently observed, can be automatically obtained by using the recent history data of the statistic information.

The minimum dispersion frame obtaining circuit 39 obtains a frame of a minimum standard deviation. Although not shown, the minimum dispersion frame obtaining circuit 39 may comprise registers for holding a frame number of a temporarily minimum standard deviation, and the temporarily minimum standard deviation, and a comparator for comparing a standard deviation of a current frame with the held standard deviation, and the minimum dispersion frame obtaining circuit 39 replace the held frame number and the standard deviation with the current frame number and the standard deviation of the current frame when the current standard deviation is not larger than the held standard deviation. When a command to indicate the frame of the minimum standard deviation which is determined by the minimum dispersion frame obtaining circuit 39 is input, the minimum dispersion frame obtaining circuit 39 sends a marker indication data to the digital scan converter 36. The marker indication data indicates how many frames before the current frame the frame of the minimum standard deviation is. When the aforementioned control circuit of the digital scan converter 36 receives the marker indication data, a marker indication is shown superimposed on the above history indication of the statistic information. FIG. 13 is a diagram showing an example indication of a frame which is designated as a frame which gives the minimum standard deviation among a plurality of frames which has been most recently observed.

Further, a histogram indicating a frequency distribution of the values of the tissue characterization parameter in a current frame can be indicated and superimposed on another histogram indicating a frequency distribution of the values of the tissue characterization parameter in the above frame of the minimum standard deviation, as shown in FIG. 14. This indication is realized by controlling the memory 35 through the frame designation circuit 38 by another output of the minimum dispersion frame obtaining circuit 39. The output of the minimum dispersion frame obtaining circuit 39 includes information of the frame of the minimum standard deviation. When the frame designation circuit 38 receives the above output, the frame designation circuit 38 receives the above output, the frame designation circuit 38 can control the frame memories 31 and 41, the scroll memory 34, and the memory 35, so that these memories output contents thereof regarding the frame of the minimum standard deviation, to the digital scan converter 36.

Otherwise, using the function of the minimum dispersion frame obtaining circuit 39, it is possible to set the ultrasonic imaging apparatus of FIG. 1 so that the apparatus automatically indicates the image of the ultrasonograph and the two-dimensional distribution image of the tissue characterization parameter of the frame of the minimum standard deviation by controlling the frame memories 31 and 41 through the frame designation circuit 38.

Although not shown, all the above operations in the embodiment can be realized by either a hardware logic circuit or software on a microcomputer.

We claim:

1. An ultrasonic imaging apparatus, comprising:
   ultrasound generating means for generating a pulsed ultrasound and externally outputting in a certain direction each pulsed ultrasound;
   ultrasound detecting means for detecting reflected ultrasound which is generated by reflection of said pulsed ultrasound at various points outside of said ultrasonic imaging apparatus in said direction and which reaches the ultrasound detecting means after output of each closed ultrasound;
   scanning means for scanning said direction of said pulsed ultrasound which is generated by said ultrasound generating means and said reflected ultrasound which reaches said ultrasound detecting means, so that a plane is scanned by the pulsed ultrasound which is generated by said ultrasound generating means during one scanning operation of said scanning means;
   two-dimensional distribution obtaining means or obtaining a two-dimensional distribution of a predetermined characteristic parameter of a medium of the ultrasound at various points in said plane, wherein distances from the ultrasound detecting means to the various points in the plane at which said reflected ultrasound are generated, are determined by measuring times which elapsed after said pulsed ultrasound is output from the ultrasound generating means until the corresponding reflected ultrasound are detected in said ultrasound detecting means;
   region of interest designating means for designating a region of interest in said plane; and
   statistical information obtaining means for obtaining statistical information on a spatial dispersion indicating how values of said predetermined characteristic parameter of the medium at various points spatially disperse in the region of interest of said plane.

2. An ultrasonic imaging apparatus according to claim 1, further comprising statistical information indicating means for indicating said statistical information.

3. An ultrasonic imaging apparatus according to claim 1, further comprising statistical information storing means for storing said statistical information for a predetermined number of planes.

4. An ultrasonic imaging apparatus according to claim 3, further comprising stored statistical information indicating means for indicating said statistical information which is stored in said statistical information storing means.

5. An ultrasonic imaging apparatus according to claim 3, further comprising two-dimensional distribution storing means for storing the two-dimensional distributions of the predetermined characteristic parameter of the medium for a predetermined number of planes.

6. An ultrasonic imaging apparatus according to claim 5, further comprising stored distribution indicating means for indicating one of said two-dimensional distributions which are stored in said two-dimensional distribution storing means.

7. An ultrasonic imaging apparatus according to claim 3, wherein said statistical information storing means stores said statistical information for a predetermined number of planes for which the two-dimensional distribution of the predetermined characteristic parameter of the medium are most recently obtained by the two-dimensional distribution obtaining means.

8. An ultrasonic imaging apparatus according to claim 7, further comprising stored statistical information indicating means for indicating said statistical information which is stored in said statistical information storing means.

9. An ultrasonic imaging apparatus according to claim 7, further comprising two-dimensional distribution storing means for storing the two-dimensional distributions of the predetermined characteristic parameter of the medium for a predetermined number of planes which are most recently obtained by the two-dimensional distribution obtaining means.

10. An ultrasonic imaging apparatus according to claim 9, further comprising stored distribution indicating means for indicating one of said two-dimensional distributions which are stored in said two-dimensional distribution storing means.

11. An ultrasonic imaging apparatus according to claim 9, further comprising storage freezing means for freezing an operation of renewing said statistical information storing means and said two-dimensional distribution storing means.

12. An ultrasonic imaging apparatus according to claim 11, further comprising frozen plane designating means for designating one of planes for which the statistical information and the two-dimensional distributions are stored in said statistical information storing means and said two-dimensional distribution storing means, respectively, after said statistical information storing means and said two-dimensional distribution storing means are frozen.

13. An ultrasonic imaging apparatus according to claim 12, further comprising designated information indicating means for indicating said statistical information and said two-dimensional distribution for the plane which is designated by said frozen plane designating means.

14. An ultrasonic imaging apparatus according to claim 9, further comprising:
   plane designating means for designating one of the planes for which the statistical information and the two-dimensional distributions are stored in said statistical information storing means and said two-dimensional distribution storing means, respectively, and
   history information indicating means for indicating a recent history of said statistical information from a plane for which the two-dimensional distribution is most recently obtained, to the plane which is designated by said plane designating means.

15. An ultrasonic imaging apparatus according to claim 9, wherein said statistical information obtaining means comprises standard deviation obtaining means for obtaining a standard deviation of said predetermined characteristic parameter of the medium at the various points in the region of interest of said plane;

said ultrasonic imaging apparatus further comprising:

minimum standard deviation plane determining means for determining a plane for which the minimum standard deviation is obtained by said standard deviation obtaining means, among planes for which the statistical information and the two-dimensional distributions are stored in said statistical information storing means and said two-dimensional distribution storing means; and minimum standard deviation plane indicating means for indicating the plane for which the minimum standard deviation is obtained by said standard deviation obtaining means.

16. An ultrasonic imaging apparatus according to claim 15, further comprising two-dimensional distribution indicating means for indicating the two-dimensional distribution for the plane for which the minimum standard deviation is obtained by said standard deviation obtaining means.

17. An ultrasonic imaging apparatus according to claim 9, further comprising:

region of interest redesignating means for designating a region of interest other than said region of interest which is designated by said region of interest designating means, in said plane; and statistical information reobtaining means for obtaining statistical information on a a dispersing characteristic of said predetermined characteristic parameter of the medium at the various points in said region of interest which is designated by said region of interest redesignating means.

18. An ultrasonic imaging apparatus according to claim 1, wherein said statistical information includes an average of values of said predetermined characteristic parameter of the medium a: the various points in the region of interest of said plane.

19. An ultrasonic imaging apparatus according to claim 1, wherein said statistical information includes a standard deviation of said predetermined characteristic parameter of the medium at the various points in the region of interest of said plane.

20. An ultrasonic imaging apparatus according to claim 1, wherein said statistical information includes a skewness of a frequency distribution of said predetermined characteristic parameter of the medium at the various points in the region of interest of said plane.

21. An ultrasonic imaging apparatus according to claim 1, wherein said statistical information includes a kurtosis of a frequency distribution of said predetermined characteristic parameter of the medium at the various points in the region of interest of said plane.

22. An ultrasonic imaging apparatus according to claim 1, wherein said statistical information includes a histogram indicating a distribution of the obtained values of said predetermined characteristic parameter of the medium at the various points in the region of interest of said plane.

23. An ultrasonic imaging apparatus for measuring a medium, comprising:

an ultrasound scanning detector sequentially providing frames of measurements indicative of a predetermined characteristic parameter at various points of the medium; and a statistical information obtaining means for statistically analyzing each frame to obtain statistical information on a a spatial dispersion indicating how values of the predetermined characteristic parameters of each frame spatially disperse in a region of interest.

24. An ultrasonic imaging apparatus according of claim 23, wherein said statistical information obtaining means further comprises means for determining a standard deviation of the statistical information of previous frames and for selecting a previous frame that has a minimum standard deviation; and wherein said apparatus further comprises a display for displaying the selected previous frame.

* * * * *

UNITED STATES PATENT AND TRADEMARK OFFICE
CERTIFICATE OF CORRECTION

PATENT NO. : 5,224,480
DATED : JULY 6, 1993
INVENTOR(S) : ISAMU YAMADA ET AL.

It is certified that error appears in the above-indentified patent and that said Letters Patent is hereby corrected as shown below:

Col. 11, line 27 (claim 1), "closed" should be --pulsed--.

Col. 13, line 42 (claim 18), "a:" should be --at--.

Signed and Sealed this

Twelfth Day of April, 1994

BRUCE LEHMAN

*Attest:*

*Attesting Officer*

*Commissioner of Patents and Trademarks*